(12) United States Patent
Walters et al.

(10) Patent No.: US 8,153,061 B2
(45) Date of Patent: Apr. 10, 2012

(54) STORAGE AND SUPPLY SYSTEM FOR CLINICAL SOLUTIONS USED IN AN AUTOMATIC ANALYZER

(75) Inventors: Jay Mark Walters, New London, PA (US); Jeannine Marie Carrio, Newark, DE (US); David Russell Thompson, Kennett Square, PA (US); Mark Richard Lloyd, Elkton, MD (US); Jeffrey Kenneth Parmer, Newark, DE (US); Richard Grear Warwick, Newark, DE (US); Thomas P. Shields, Wayne, MI (US); Lawrence D. Huppman, Newark, DE (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 1009 days.

(21) Appl. No.: 11/560,220

(22) Filed: Nov. 15, 2006

(65) Prior Publication Data

US 2007/0116599 A1    May 24, 2007

Related U.S. Application Data

(60) Provisional application No. 60/739,899, filed on Nov. 23, 2005.

(51) Int. Cl.
*G01N 35/00* (2006.01)
(52) U.S. Cl. ............... 422/64; 422/63; 422/561; 436/43
(58) Field of Classification Search .......... None
See application file for complete search history.

(56) References Cited

U.S. PATENT DOCUMENTS

| 4,070,156 | A | 1/1978 | Moran et al. |
| D296,668 | S | 7/1988 | Stavish |
| 5,075,082 | A | 12/1991 | Fechtner |
| 5,158,748 | A | 10/1992 | Obi et al. |
| D332,544 | S | 1/1993 | Seiner et al. |
| D342,140 | S | 12/1993 | Sakagami et al. |
| 5,294,404 | A | 3/1994 | Grandone et al. |
| D358,219 | S | 5/1995 | Ushikubo |
| 5,434,083 | A | 7/1995 | Mitsumaki et al. |
| 5,827,586 | A | 10/1998 | Yamashita et al. |
| D407,826 | S | 4/1999 | Yamazchi et al. |
| 5,898,113 | A | 4/1999 | Vicere |
| 5,899,334 | A | 5/1999 | Domerchie et al. |
| 6,019,945 | A | 2/2000 | Ohishi et al. |
| 6,070,723 | A | 6/2000 | Lewis |

(Continued)

FOREIGN PATENT DOCUMENTS

JP           55-143566           * 10/1980

(Continued)

OTHER PUBLICATIONS

English Abstract of JP H08-271525A.

(Continued)

*Primary Examiner* — P. Kathryn Wright
(74) *Attorney, Agent, or Firm* — Leland K. Jordan

(57) ABSTRACT

A fluid handling system adapted to provide storage and supply of a number of liquid solutions to an automatic clinical analyzer having three different bottle-like containers, a collapsible plastic-metal-plastic pouch having a mouth-like opening, a fitment to be sealed within mouth-like opening a septum within the fitment, and open meal band or cap to seal the septum into the fitment.

8 Claims, 19 Drawing Sheets

U.S. PATENT DOCUMENTS

| | | | |
|---|---|---|---|
| 6,090,630 A | 7/2000 | Knakutshu et al. | |
| 6,178,832 B1 | 1/2001 | Mathur et al. | |
| 6,364,472 B1 | 4/2002 | Hmelar et al. | |
| 6,418,800 B1 | 7/2002 | Mathur et al. | |
| D480,630 S | 10/2003 | Berman | |
| D504,323 S | 4/2005 | Berman | |
| 2004/0005714 A1* | 1/2004 | Safar et al. | 436/43 |
| 2005/0035156 A1* | 2/2005 | Hersch et al. | 222/504 |

FOREIGN PATENT DOCUMENTS

| | | |
|---|---|---|
| JP | S58-501367 A | 8/1983 |
| JP | H08-105900 A | 4/1996 |
| JP | H08-271525 A | 10/1996 |
| JP | H10-58701A A | 3/1998 |
| JP | H11-133032 A | 5/1999 |
| WO | 83/00932 A | 4/1996 |

OTHER PUBLICATIONS

English Abstract of JP H11-133032A.
English Abstract of JP H10-58701A.
English Abstract of JP H08-105900A.

* cited by examiner

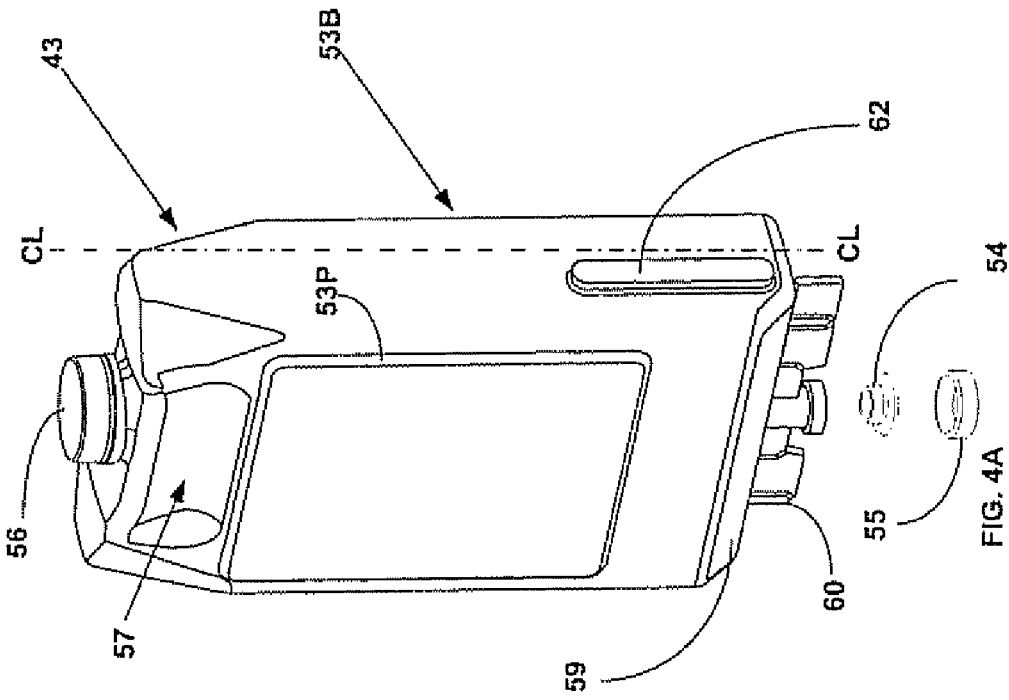
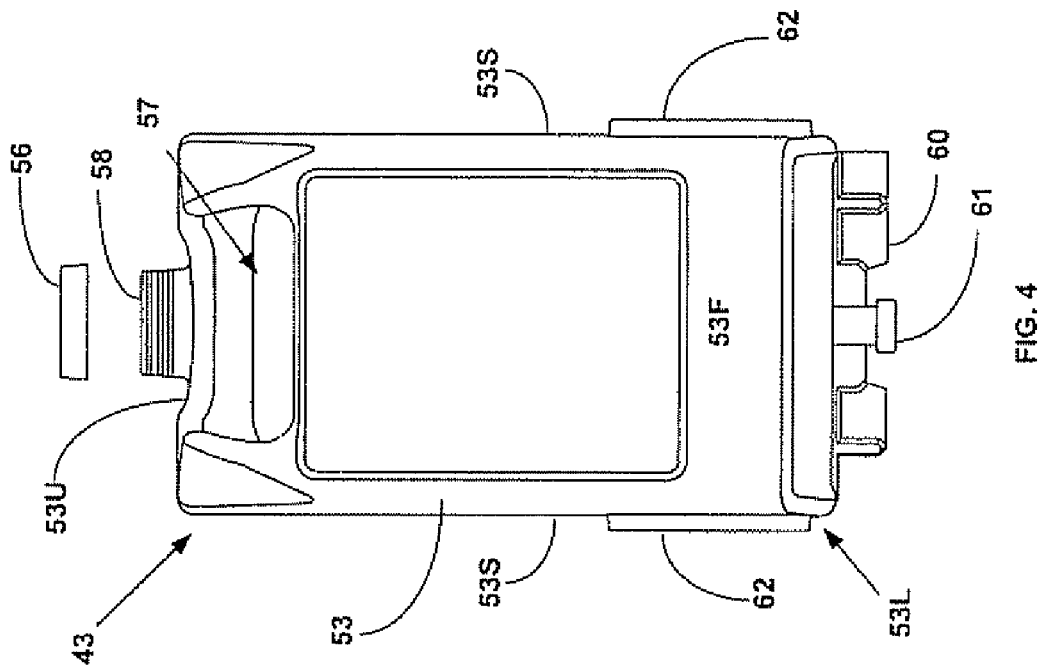

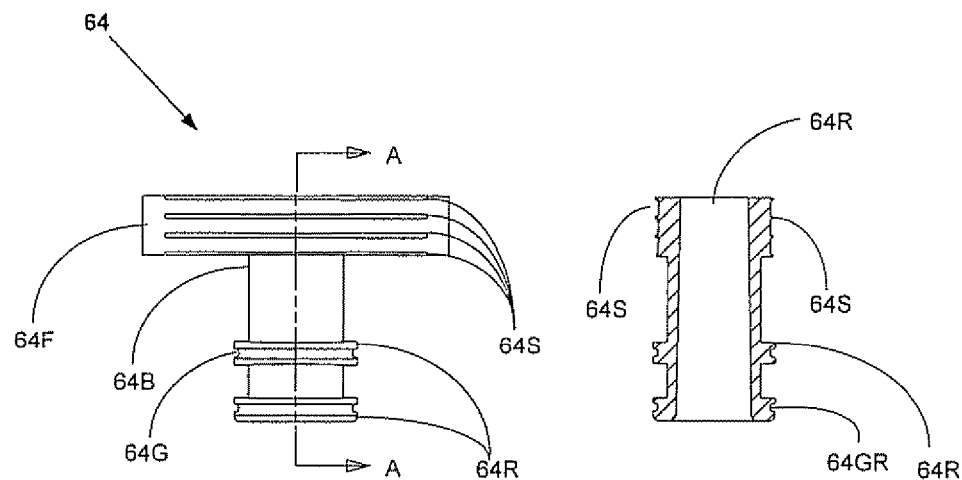
FIG. 10
FIG. 10A
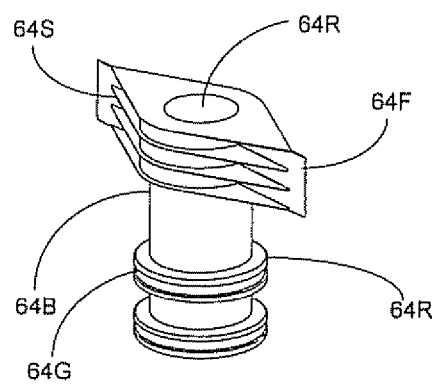
FIG. 10C
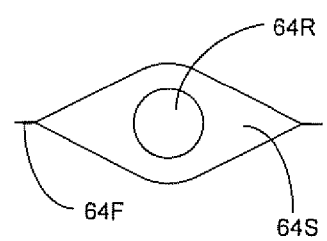
FIG. 10D

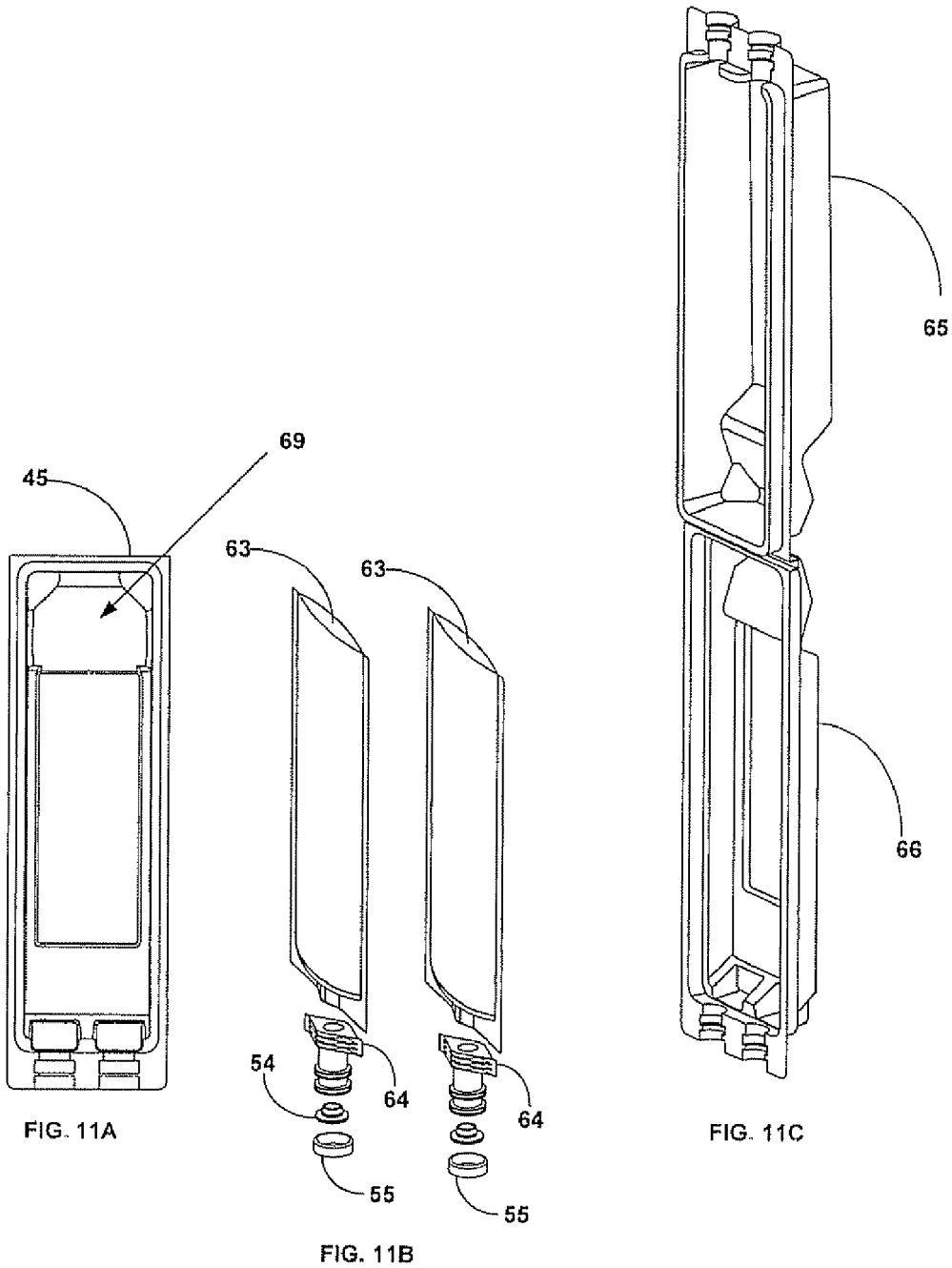

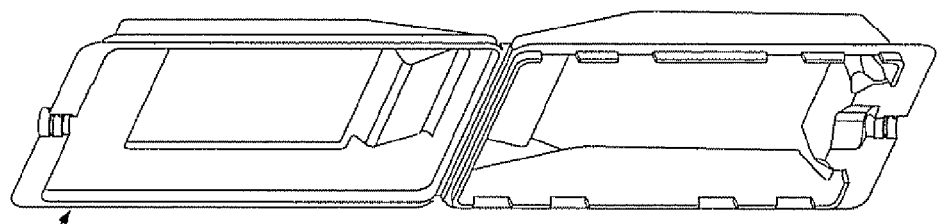
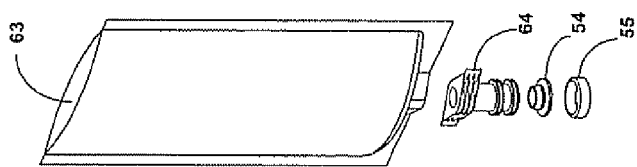
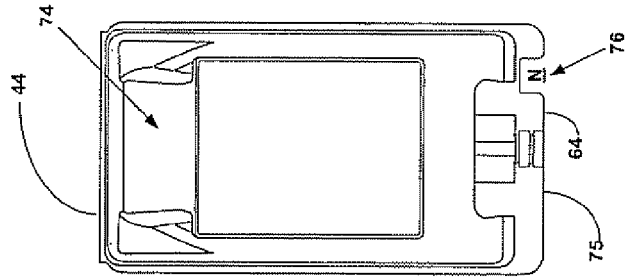

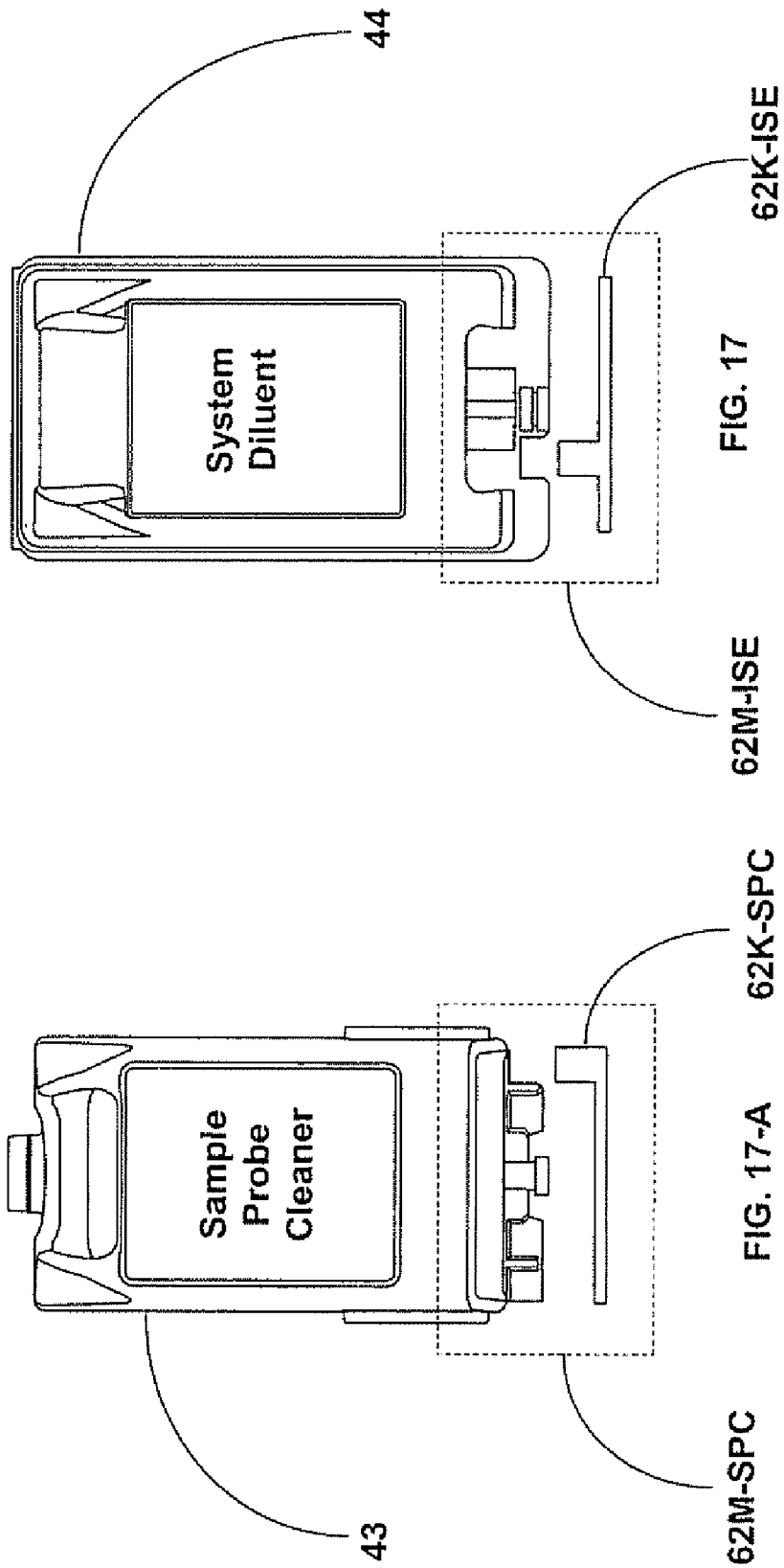

STORAGE AND SUPPLY SYSTEM FOR CLINICAL SOLUTIONS USED IN AN AUTOMATIC ANALYZER

RELATED APPLICATION INFORMATION

This Application claims priority from Provisional Application No. 60/739,899, filed Nov. 23, 2005.

FIELD OF THE INVENTION

The present invention relates to a solution supply system for use in a clinical analyzer capable of automatically processing a patient's biological fluid samples such as urine, blood serum, plasma, cerebrospinal fluid and the like. In particular, the present invention provides a fluid handling system for an automatic clinical analyzer with a number of liquid solution storage and supply containers having features to ensure proper installation.

BACKGROUND OF THE INVENTION

Various types of tests related to patient diagnosis and therapy can be performed by analysis of a sample taken from a patient's infections, bodily fluids or abscesses. These assays typically involve automated analyzers onto which vials containing patient samples have been loaded. The analyzer extracts the samples from the vials and combines the samples with various reagents in special reaction cuvettes or tubes. Frequently, the samples are incubated or otherwise processed before being analyzed. Analytical measurements are often performed using a beam of interrogating radiation interacting with the sample-reagent combination, for example turbidimetric, fluorometric, absorption readings or the like. The measurements allow determination of end-point or rate values from which an amount of analyte may be determined using well-known calibration techniques.

Clinical sample analysis continuously needs to be more effective in terms of providing an increased number of advanced analytical options so as to enhance a laboratory's techniques for evaluating patient samples. Luminescent compounds, such as fluorescent compounds and chemiluminescent compounds, find wide application in the assay field because of their ability to emit light. Particles, such as latex beads and liposomes, have also been utilized in assays. For example, in homogeneous assays an enzyme may be entrapped in the aqueous phase of a liposome labeled with an antibody or antigen. Homogeneous immunoassays in which it is unnecessary to separate the bound and unbound label have previously been described for small molecules. These assays include enzyme channeling immunoassay, and fluorescence energy transfer immunoassay enzyme inhibitor immunoassays; fluorescence polarization immunoassay among others.

In view of this number of available analytical detection techniques, a modern clinical analyzer may include multiple detection units, each detection unit adapted to perform different measurements and follow various analysis protocols that the other detection units. The diversity of analytical detectors allows multiple types of tests to be run on the same system, thereby increasing the likelihood that an analyte can be determined by an assay that is most appropriate for that particular analyte, e.g., an assay that is highly specific for the analyte, is accomplished in a reasonable period of time, and is cost effective. In particular, an analyzer may include a detector adapted to detect luminescence of a reaction mixture in a reaction vessel as well as a photometer or turbidometer detector as well as a nephelometer detector as well as a yet another, different type of detector, such as an ion selective electrode, identified hereinafter as "ISE". Clearly, accurately supplying the various different reagents required for such a range of different analytical detectors is an important aspect of maintaining analyzer throughput.

SUMMARY OF THE INVENTION

The present invention provides a basic fluid storage system comprising a basic fluid storage system and ISE fluid storage system. The basic fluid storage system supports the sample and reagent probe cleaners, system diluent, and cuvette wash solution. Individual compartments are provided to house the four consumables. Each compartment is physically keyed to prevent the installation of an incorrect fluid. Each consumable will be bar coded prior to installation. Common to each compartment is a manifold with a replaceable probe for piercing the septum of each consumable. The fluids are then gravity fed into reservoirs which are controlled by two position level sensors. A filtered vent is provided to allow fluid flow. The vent is positioned above the consumable to guard against leakage in the event the valve fails open. The instrument operating system will alert the operator that a fluid will run out and has run out. The fluids are delivered to their respective destinations through tubing harnesses.

The ISE fluid storage system supports the ISE diluent, ISE standard A, ISE standard B, and ISE salt bridge consumables. Compartments are provided to house the four consumables. Standard B and salt bridge are contained within the same compartment. Each compartment is physically keyed to prevent the installation of an incorrect fluid. Each consumable will be bar coded prior to installation. Common to each consumable is a replaceable probe for piercing the septum of each consumable. Fluid counters in the instrument operating system will keep track of the amount of fluid used in each consumable. The instrument operating system will alert the operator that a fluid will run out and has run out. The fluids are delivered to their respective destinations through a tubing harness.

BRIEF DESCRIPTION OF THE DRAWINGS

The invention will be more fully understood from the following detailed description thereof taken in connection with the accompanying drawings which form a part of this application and in which:

FIG. 4 is a front elevation view of the bottle-like container providing bulk storage and supply of sample and reagent probe cleaning solutions and cuvette wash solution;

FIG. 4A is a perspective view of the bottle-like container of FIG. 4;

FIGS. 10, 10A, 10C, 10D are front, section, perspective and top views of a fitment useful with the pouch of FIG. 9;

FIG. 11A is a front elevation view of the bottle-like container providing bulk storage and supply of salt bridge and second standard solution;

FIG. 11B is an exploded perspective view of two solution pouches of FIG. 9 used in the bottle-like container of FIG. 11A;

FIG. 11C is an perspective view of the bottle-like container of FIG. 11A in an opened form;

FIG. 13A is a front elevation view of the bottle-like container providing bulk storage and supply of first and second diluent solutions, and first standard solution;

FIG. 13B is an exploded perspective view of a solution pouch of FIG. 9 used in the bottle-like container of FIG. 13A;

FIG. 13C is an perspective view of the bottle-like container of FIG. 13A in an opened form;

FIGS. 17 and 17-A further illustrates two different bottle-like containers of FIG. 2 in respectively different keyed brackets of FIG. 6;

DETAILED DESCRIPTION OF THE INVENTION

Figure 1:
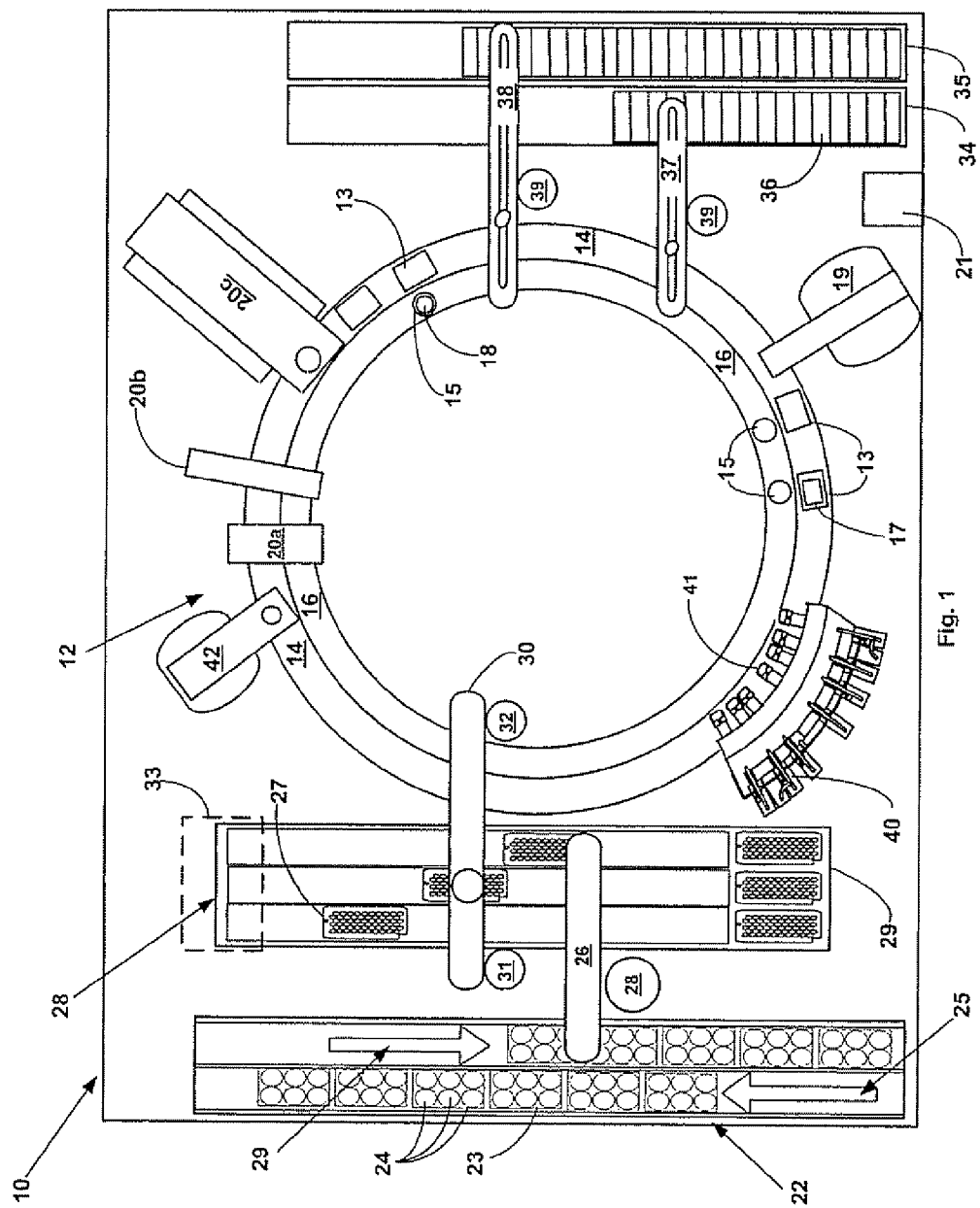
FIG. 1 is a schematic plan view of an automated analyzer in which the present invention may be employed to advantage.

FIG. 1 shows schematically the elements of an automatic chemical analyzer 10 comprising a reaction carousel 12 supporting an outer cuvette circle 14 having generally rectangular cuvette ports 13 formed therein and an inner cuvette ring 16 having generally circular vessel ports 15 formed therein. Cuvette ports 13 are adapted to receive a plurality of reaction cuvettes 17 like disclosed in co-pending application Ser. No. 09/949,132 assigned to the assignee of the present invention and containing various reagents and sample liquids for conventional clinical and immunoassay assays while vessel ports 15 are adapted to receive a plurality of reaction vessels 18 that contain specialized reagents for ultra-high sensitivity luminescent immunoassays. Reaction carousel 12 is rotatable using stepwise movements in a counterwise direction, the stepwise movements being separated by a constant dwell time during which carousel 12 is maintained stationary and computer controlled assay operational devices 19, such as sensors, sample and reagent add stations, sample and reagent probe washing stations and the like, operate as needed on an assay mixture contained within cuvettes 17 and reaction vessels 18. In an exemplary embodiment, analyzer 10 includes multiple detector units 20a, 20b, 20c, each detection unit 20a, 20b, and 20c being adapted to perform different clinical analytical measurements and follow various analysis protocols different from the other detection units. The samples and reaction mixture may be analyzed in the cuvettes 17, 18 while in their respective carousels 14, 16, or may be moved into the detection units 20a, 20b, and 20c by a conventional cuvette transporter (not shown).

Analyzer 10 is controlled by software executed by the analyzer operating computer 21 based on computer programs written in a machine language like that used on the Dimension® clinical chemistry analyzer sold by Dade Behring Inc, of Deerfield, Ill., and widely used by those skilled in the art of computer-based electromechanical control programming. Computer 21 also executes application software programs for performing assays conducted by various detector units 20a, 20b, and 20c within analyzer 10.

As seen in FIG. 1, a bidirectional incoming and outgoing sample fluid tube transport system 22 comprises a mechanism for transporting sample fluid tube racks 23 containing open or closed sample fluid containers such as sample fluid tubes 24 from a rack input load position at a first end of an input lane to the second end of input lane as indicated by open arrow 25. Liquid specimens contained in sample tubes 24 are identified by reading bar coded indicia placed thereon using a conventional bar code reader to determine, among other items, a patient's identity, tests to be performed, if a sample aliquot is to be retained within analyzer 10 and if so, for what period of time. It is also common practice to place bar coded indicia on sample tube racks 23 and employ a large number of bar code readers installed throughout analyzer 10 to ascertain, control and track the location of sample tubes 24 and sample tube racks 23.

A conventional liquid sampling probe 26 is located proximate sample output lane indicated by open arrow 29 and is operable to aspirate aliquot portions of sample fluid from sample fluid tubes 24 and to dispense an aliquot portion(s) of the sample fluid into one or more of a plurality of wells in an aliquot vessel array 27 depending on the quantity of sample fluid required to perform the requisite assays and to provide for a sample fluid aliquot to be retained by analyzer 10 within an environmental storage chamber 33. After sample fluid is aspirated from all sample fluid tubes 24 on a rack 23 and dispensed into aliquot vessel arrays 27 maintained in an aliquot vessel array storage and transport system 28, the liquid sampling probe 26 is washed within a probe washing station 28 using sample probe wash solution supplied by the fluid handling system of the present invention. Rack 23 is removed from analyzer 10 in the direction indicated by arrow 29.

Aliquot vessel array transport system 28 comprises an aliquot vessel array storage and dispensing module 29 adapted to bi-directionally translate aliquot vessel arrays 27 within a number of aliquot vessel array tracks below a sample aspiration needle probe 30 located proximate reaction carousel 12. Sample aspiration probe 30 is controlled by computer 21 to optionally aspirate assay diluent from diluent station 31 supplied by the fluid handling system of the present invention and dispense a controlled amount of diluent into one or more cuvettes 17 prior to testing. Sample aspiration probe 30 is further controlled by computer 21 and is adapted to aspirate a controlled amount of sample from individual wells within an aliquot vessel array 27 positioned at a sampling location within a track and is then shuttled to a dispensing location where an appropriate amount of aspirated sample is dispensed into one or more cuvettes 17, 18 for testing by analyzer 10 for one or more analytes. Subsequent to dispensing sample into cuvettes 17, 18, probe 30 is washed within a probe washing station 32 using the sample probe wash solution supplied by the fluid handling system of the present invention. After sample has been dispensed into reaction cuvettes 17, 18, conventional transfer means move aliquot vessel arrays 27 as required between aliquot vessel array transport system 27, environmental storage chamber 33 and a disposal area (not shown).

Temperature-controlled storage areas or servers 34 and 35 inventory a plurality of multi-compartment elongate reagent cartridges 36 described in co-pending application Ser. No. 09/949,132 assigned to the assignee of the present invention, containing reagents as necessary to perform a number of different assays.

Reagent aspiration needle probes 37, 38 are independently mounted and translatable between servers 34 and 35, respectively, and cuvette carousels 14, 16. Aspiration probes 37, 38 comprise conventional mechanisms for aspirating reagents required to conduct specified assays at a reagenting location from wells in appropriate reagent cartridges 36, the probes 37, 38 subsequently being shuttled to a dispensing location where reagents are dispensed into cuvettes 17, 18 and then washed within reagent probe washing stations 39 using a special reagent probe wash solution supplied by the fluid handling system of the present invention.

For reasons of reducing the cost-per-reportable result, it is advantageous that used cuvettes 17 be washed in a cuvette wash station 40 and replaced into ports 13 to be re-cleaned after being used on subsequent reaction assays. Wash station 40 comprises a number of washing, drying manifolds, and waste manifolds. The washing manifolds are in fluid communication with a washing probe 41 and a source of cuvette wash solution supplied by the fluid handling system of the present invention.

During operation of analyzer 10, various reagents and/or cleaning solutions may be consumed in so-called bulk quantities as opposed to relatively minute quantities of reagents supplied in multi-compartment elongate reagent containers like illustrated in U.S. Pat. No. 6,943,030 and containing reagents necessary to perform a given assay within a number of wells, each well containing as little as 3.4 mL of a given reagent and calibration vial containers containing similar quantities of calibration solutions used to conduct well-know calibration and quality control procedures within analyzer 10.

Figure 2:
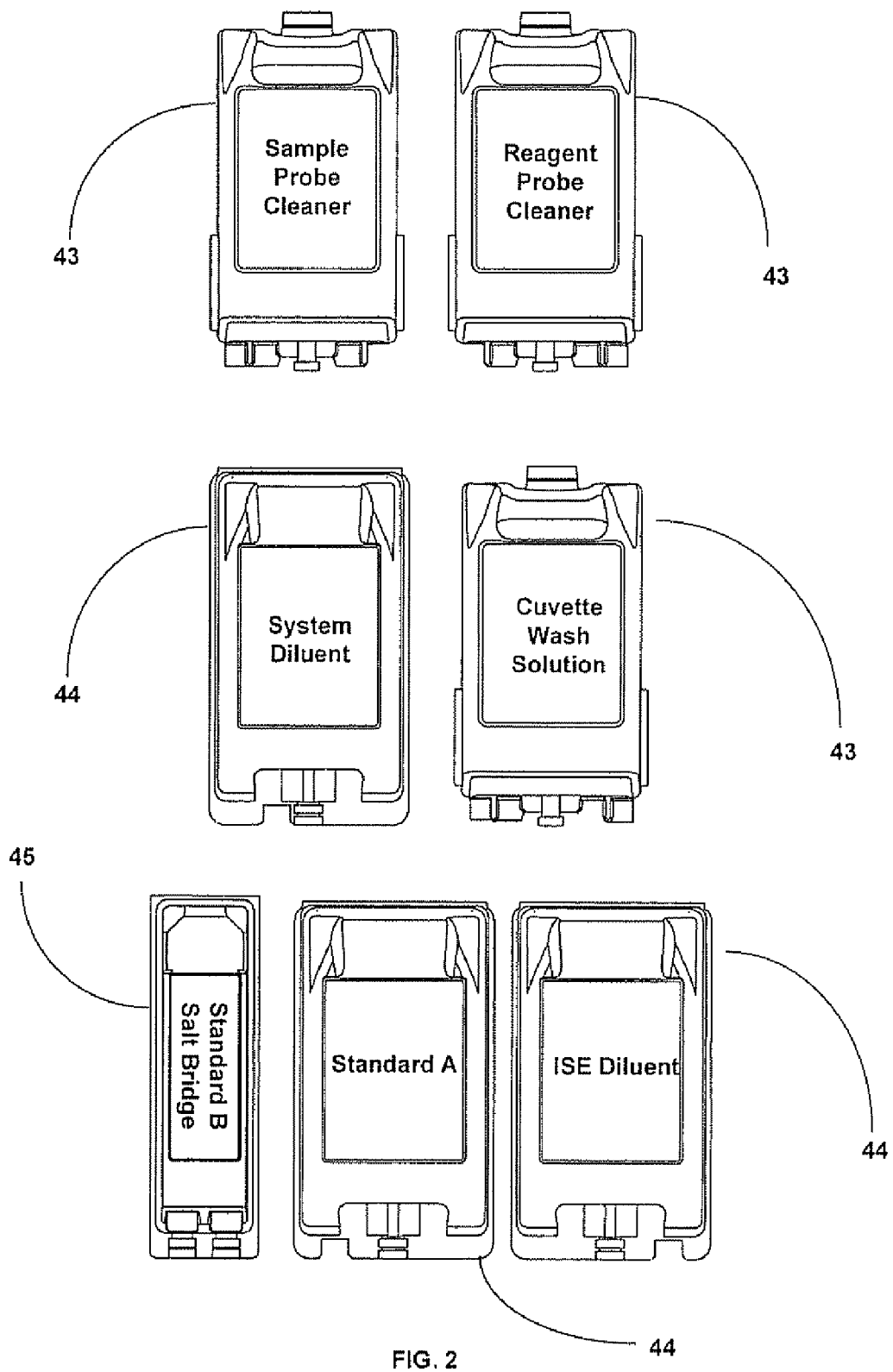
FIG. 2 is a front view of three different bottle-like containers of the present invention, wherein the different bottle-like containers provide bulk storage and supply of sample and reagent probe cleaning solutions, first and second diluent solutions, a cuvette wash solution, first and second standard solutions, and a salt bridge solution.
Figure 3:
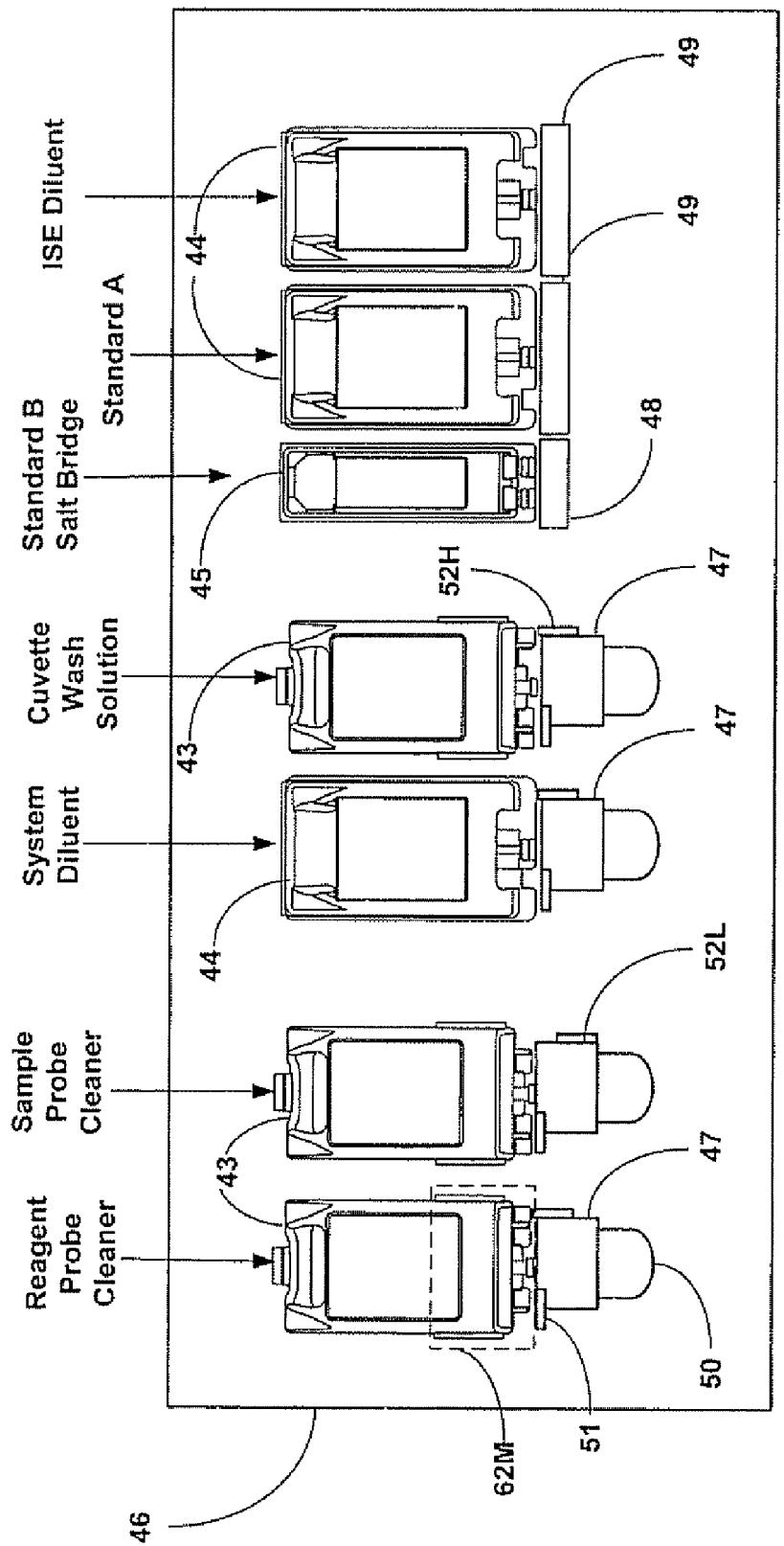
FIG. 3 is a view of the three different bottle-like containers of FIG. 2 mounted within a clinical analyzer.

In particular, operation and calibration of an ion selective electron (ISE) detector 42 located proximate carousel 12 requires relatively large quantities of a first standard solution and a diluent and relatively smaller quantities of both a second standard solution and of a so-called "salt bridge". Further, as described above, in routine operation of analyzer 10, relatively large bulk quantities of solutions formulated to wash cuvettes, reagent and sample probes and a system diluent are required. The purpose of the fluid handling system of the present invention is to provide storage and supply of an ISE diluent, first and second standard solutions, and a salt bridge, as well as storage and supply of a cuvette wash solution, a system diluent, a sample probe cleaner, and a reagent probe cleaner. For purposes of controlling manufacturing costs and for simplicity in system operation, three different bottle-like containers like illustrated in FIG. 2 are provided wherein bottle-like containers 43 provide bulk storage and supply of cuvette wash solution and sample and reagent probe cleaning solutions. Clam-shelf-like thermoformed containers 44 provide storage and supply of ISE first standard A solution and ISE diluent solution, and of a system diluent solution and dual chamber clam-shell-like thermoformed container 45 provides storage and supply of an ISE second standard B solution and salt bridge. FIG. 3 illustrates the three different bottle-like containers 43, 44 and 45 mounted inside a front panel 46 of analyzer 10 in a preferred arrangement, bottle-like containers 43, 44 positioned above a fluid manifold 47 described hereinafter and bottle-like containers 44, 45 positioned above a single-position manifold 48 and a two-position manifold 49 described hereinafter. Bottle-like containers 43, 44 comprise a series of features that ensure that the appropriate solution bottle is correctly placed into the corresponding location on panel 46 and are key feature of the bulk fluid storage system of the present invention.

ISE Standards A and B and the ISE Diluent comprise controlled quantities of $Na^+$, $K^+$, surfactant, preservative and a buffer; the Salt Bridge comprises controlled quantities of $K^+$, $Cl^-$, surfactant, and a preservative; ISE Diluent comprises controlled quantities of $Na^+$, $Cl^-$, surfactant, preservative and a buffer; System diluent comprises controlled quantities of phosphate buffered saline and a preservative; Cuvette Wash Fluid comprises controlled quantities of a surfactant, a preservative and a buffer; Reagent Probe Cleaner comprises 0.1 N Sodium Hydroxide; and Sample Probe Cleaner comprises 5% Sodium Hypochlorite. In order to properly operate analyzer 10, it is critical that containers 44 containing system diluent, ISE first standard A solution and ISE diluent solution be placed only in locations marked "System Diluent", "ISE Standard A" and "ISE Diluent", respectively; it is further critical that containers 43 containing cuvette wash solution and sample and reagent probe cleaning solutions be placed only in locations marked "Cuvette Wash Solution", "Sample Probe Cleaner" and "Reagent Probe Cleaner", respectively; and how it is further critical that containers 45 containing ISE second standard solution and ISE salt bridge solution be placed only in locations marked "ISE Standard B" and "ISE Salt Bridge", respectively. As mentioned previously, however, for cost-containment reasons, it is advantageous to have similarly shaped liquid solution containers wherever possible, and therefore precautions must be employed to insure that the proper liquid solution container is placed in the proper location.

Bottle containers 43 are preferably extrusion blow molded high-density polyethylene with density greater than or equal to 0.941 g/cc with blue-white colorant with a 0.030 in. nominal wall thickness and are adapted to provide storage and supply of sample and reagent probe cleaning solutions and cuvette wash solutions while mounted on panel 46 of analyzer 10 by employing gravity feed of solutions through manifold 47 into a reservoir 50 equipped with inlet valves 51 and low and high level sensors 52, container 43 adapted to be replenished while analyzer 10 is running while the manifold 47, reservoir 50, valves 51 and low and high level sensors 52L and 52H, respectively, cooperate to maintain a supply of solution to sample and reagent probe cleaning stations. In operation, Based on monitored consumption, analyzer operating computer 21 prompts an operator to install a new sample probe or reagent probe or cuvette wash solution container 43.

Analyzer operating computer 21 opens consumable inlet valve 51.

Analyzer operating computer 21 delays a one minute waiting period for the low level sensor 52L to change state from 5V (no liquid present) to 0V (liquid present). If the fluid level fails to rise and change the state of sensor 52L, an error message is displayed.

Once the one minute waiting period is completed, a second timer is started. There is a five minute waiting period for the high level sensor 52H to change state from 5V (no liquid present) to 0V (liquid present). If the fluid level fails to rise and change the state of the high sensor, an error message is displayed and the inlet valve is closed.

When fluid covers the high sensor 52H the sensor output switches to 0V.

Analyzer operating computer 21 closes the inlet valve 51.

Analyzer operating computer 21 runs a prime cycle.

Fluid level lowers due to assay processing by analyzer 10.

Analyzer operating computer 21 delays a period of sixty minutes before checking the high level sensor.

When fluid level no longer covers high level sensor the sensor output switches to 5V.

Analyzer operating computer 21 opens inlet valve.

Analyzer operating computer 21 delays a five minute period for the high level sensor 52H to change state from 5V (no liquid present) to 0V (liquid present). If the fluid level fails to rise and change the state of the high level sensor 52H, a message is displayed prompting the user that the consumable is empty and should be replaced. Typically, one day of processing is available in the fluid reservoir before assay processing is affected.

Figure 5:
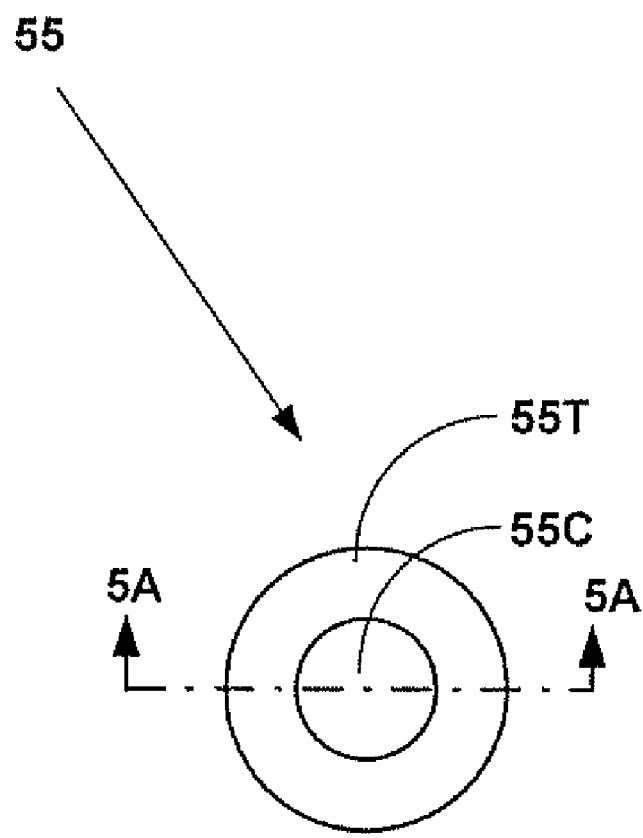
FIG. 5 is plan view of a cap useful in the present invention.
Figure 5A:
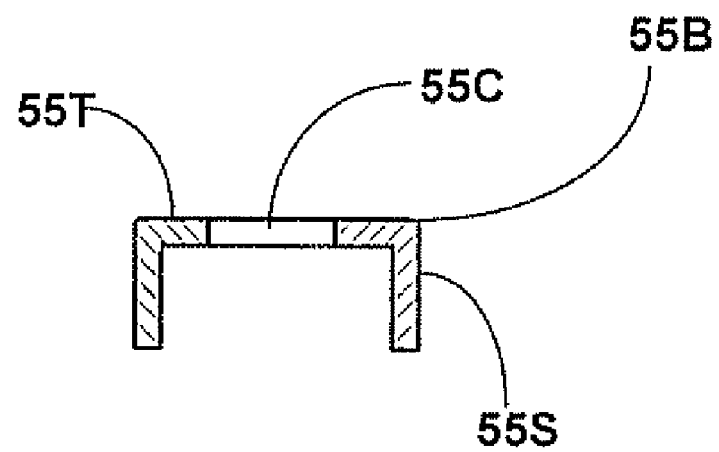
FIG. 5A is section view of the cap of FIG. 5 along the line A-A.
Figure 6:
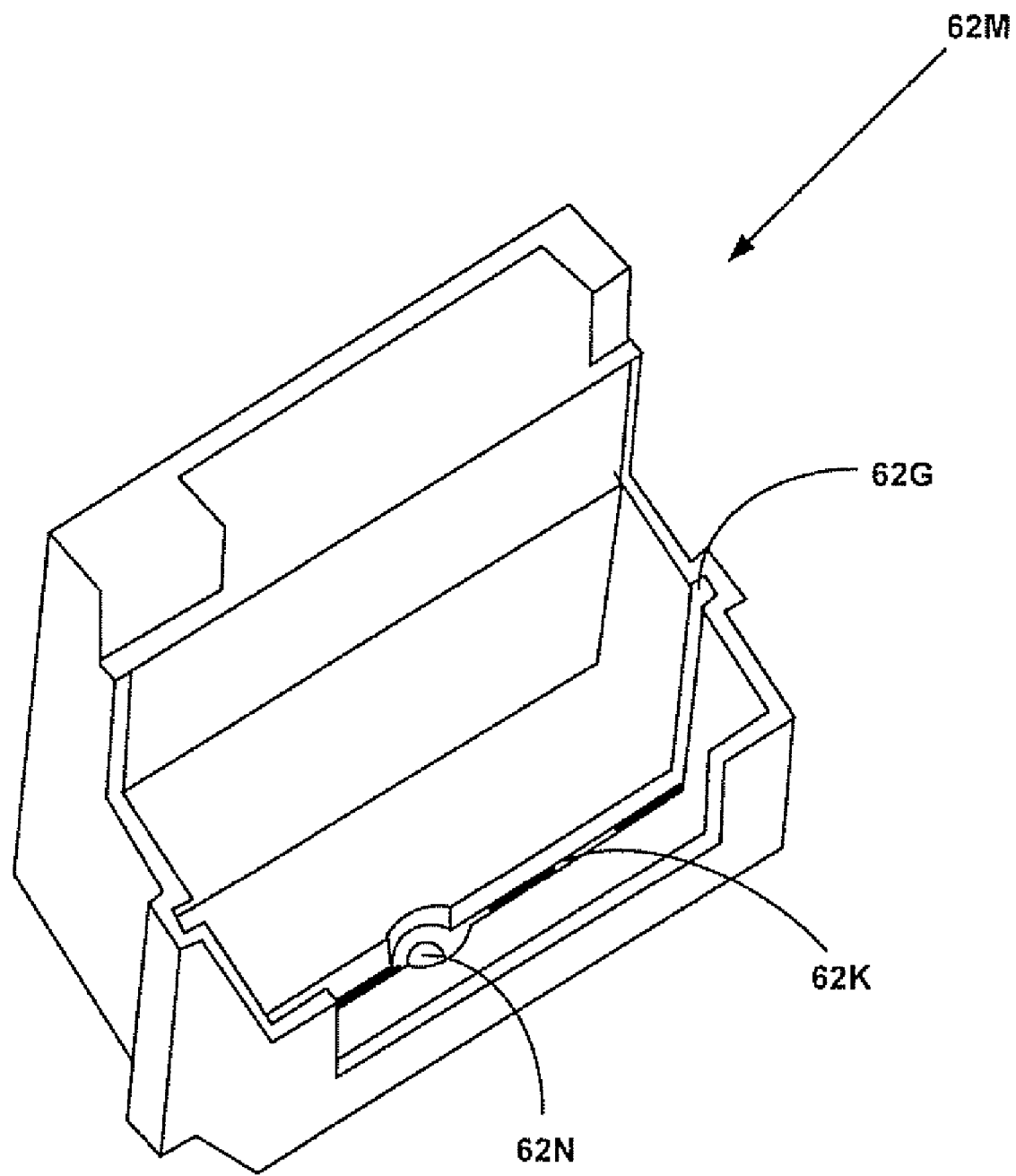
FIG. 6 is a perspective view of an analyzer bracket keyed to accept one of the bottle-like containers of the present invention.

Bottle-like container 43 is illustrated in FIG. 4, a front view, and FIG. 4A a perspective, as comprising a hollow body 53, a penetratable septum 54, an open metal band or cap 55 and a threaded cap 56. Body 53 comprises an opposed front 53F and back 53B connected by opposed sides 53S, body 53 having a user-friendly recessed handle area 57 and a threaded opening 58 in the upper portion 53U thereof that can be closed by mating threaded cap 56. The lower portion 53L of body 53 has a front tapered portion 59 with a mounting fin 60 and a pipe-like opening 61 depending therefrom. In an exemplary embodiment, fin 60 is notched in one of several patterns, each pattern keyed for a selected sample and reagent probe cleaning solution and cuvette wash solution. Pipe-like opening 61 is closed with penetratable septum 54 and open cap 55, open cap 55 having an central opening 55C formed in a round top 55T having a circumferential side 55S depending therefrom (FIGS. 5 and 5A), central opening 55C having an inner beveled circumference 55B. A pair of alignment ridges 62 extend outwardly from the sides 53S of body 53 in the lower portion 53L of body 53, alignment ridges 62 sized to fit into corresponding grooves 62G formed in a mounting bracket 62M (seen in dashed lines for purposes of clarity in FIG. 3) on front panel 26 of analyzer 10 in such a manner that septum 54 is pierced by needle 62N (FIG. 6). Front 53F optionally comprises a slightly raised panel 53P suitable for affixing an identifying color-coded, sticker-like label, the label being color-coded to match coloring on panel 26 to assist an operator in correctly placing bottle containers 43 into appropriate mounting brackets 62M. Another important feature of the present invention is the positioning of alignment ridges 62, fin 60, and pipe-like opening 61 between the side centerline CL and the front 53F of body 53. FIG. 6 further illustrates a mating key 62K having a pattern of closed and open sections that match only one of a number of corresponding keyed patterns notched in fin 60 in a number of corresponding keyed patterns, each pattern keyed for a selected solution as explained below. This feature of container 43 acts to further ensure that the appropriate bottle container 43 is correctly oriented when placed into appropriate bracket 62P on analyzer 10. If an operator attempted to insert an appropriate bottle container 43 into an appropriate mounting bracket 62M on analyzer 10 but container 43 was "backwards" or reversed front-to-back, the back 53B of bottle container 43 would extend too great a distance from alignment ridges 62 to allow the container 43 to be placed into mounting bracket 62P because of a mechanical interference.

Figure 7A:
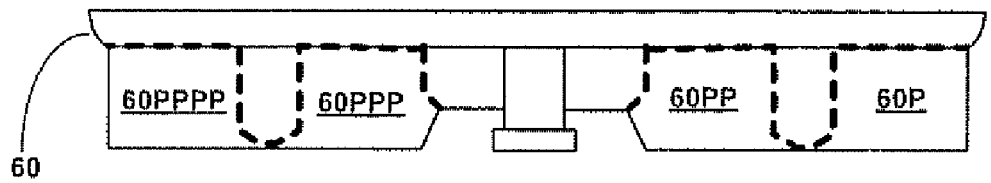
FIGS. 7A-E illustrates several key patterns useful on the bottle-like containers of FIG. 4.
Figure 7B:
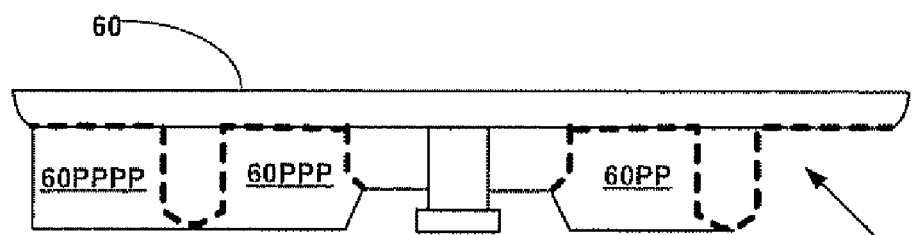
Figure 7C:
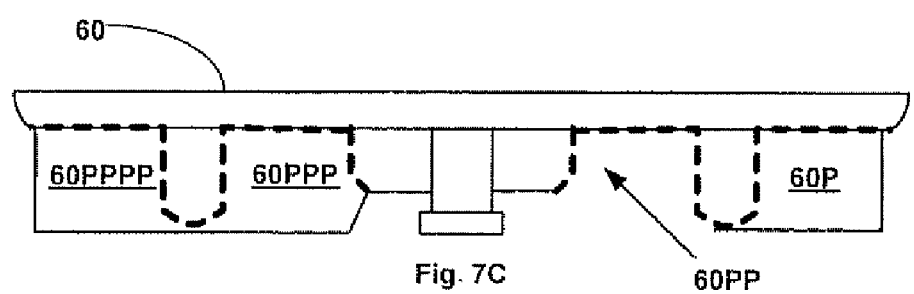
Figure 7D:
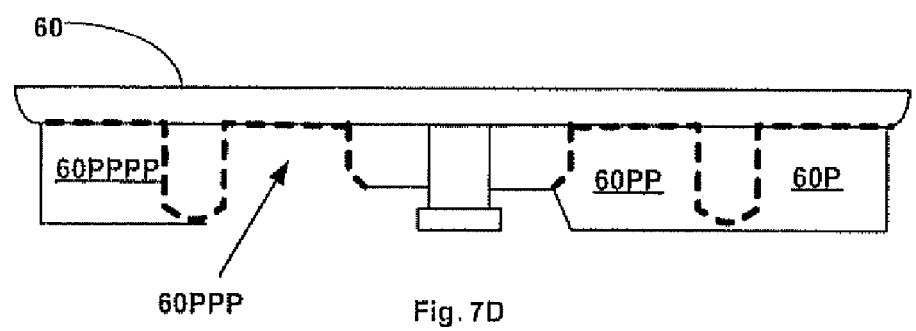
Figure 7E:
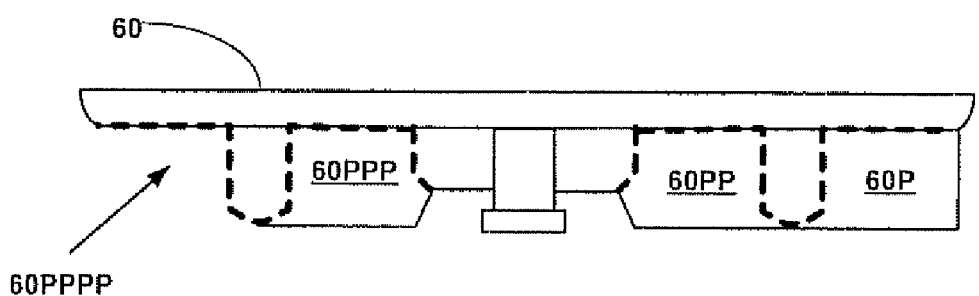

As mentioned previously, a key feature of the fluid handling system of the present invention in ensuring that the appropriate bottle container 43 is correctly oriented when placed into appropriate mounting bracket 62M on analyzer 10 is a notching of fin 60 in one of three or four notched patterns, each pattern keyed for a selected solution, mounting bracket 62M having the corresponding keyed pattern so that the only bottle container 43 that can be mounted in mounting bracket 62M has its fin 60 notched in a pattern that corresponds to the mating key pattern 62K. FIG. 7A illustrates fin 60 as comprising a removable first portion 60P having a removable second portion 60PP next adjacent thereto, second portion 60PP having a removable third portion 60PPP next adjacent thereto, and third portion 60PPP having a removable fourth portion 60PPPP next adjacent thereto FIGS. 7B-C-D-E illustrate one embodiment of this keyed pattern as comprising a first pattern wherein a first portion 60P of fin 60 of container 43 is removed (FIG. 7B, for example for containers 43 containing sample probe cleaner solution) and a second pattern wherein a second portion 60PP, next adjacent to first portion 60P of fin 60 is removed, the first portion 60P remaining intact (FIG. 7C, for example cuvette wash solution) and a third pattern wherein a third portion 60PPP next adjacent to second portion 60PP of fin 60 is removed, the first portion 60P and the second portion 60PP remaining intact (FIG. 7D for example for a future clinical solution) and a fourth pattern wherein a fourth portion 60PPPP next adjacent to third portion 60PPP of fin 60 is removed, the first portion 60P and the second portion 60PP and the third portion 60PPP remaining intact (FIG. 7E, for example for a reagent probe cleaner solution). Line 60L represents a groove on both sides of fin 60 molded into fin 60 in order to facilitate removal of first portion 60P, second portion 60PP, third portion 60PPP and fourth portion 60PPPP. Those skilled in the art will readily appreciate that other keyed patterns may be selected for fin 60, and that the removal of portions 60P, 60PP, 60PPP, and 60PPPP may be altered without departing from the scope of the invention. In the embodiment shown, all of portions 60P, 60PP, 60PPP, and 60PPPP were removed sequentially. However, in alternate embodiments, selected ones of portions 60P, 60PP, 60PPP, and 60PPPP may be removed without departing from the scope of the invention.

Figure 8A:
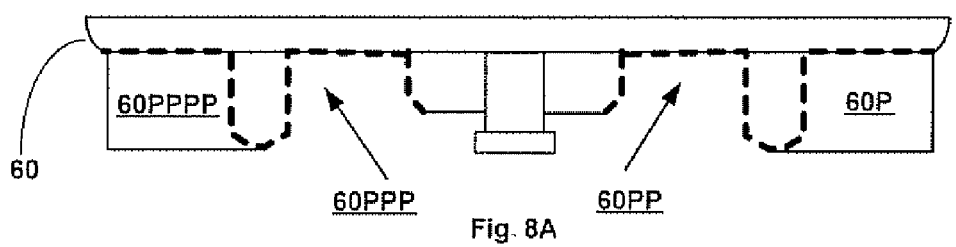
FIGS. 8A-B illustrates alternate key patterns useful on the bottle-like containers of FIG. 4.
Figure 8B:
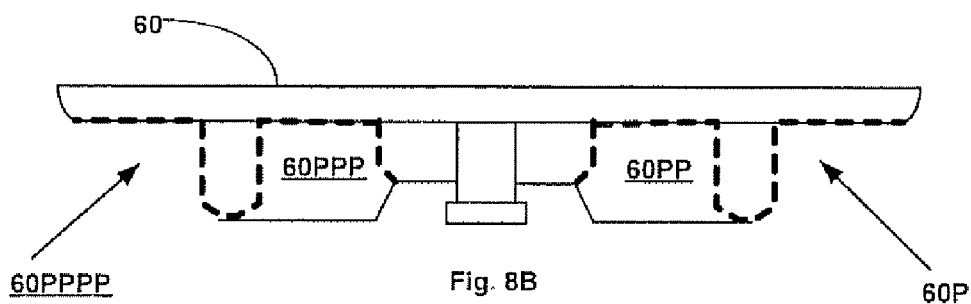

For example, in the embodiment shown in FIGS. 8A and 8B, the keyed pattern is seen as comprising a first pattern wherein only but both second portion 60PP and third portion 60PPP of fin 60 are removed and a second pattern wherein only but both first portion 60P and fourth portion 60PPPP are removed.

The purpose of the fluid handling system of the present invention is to provide storage of and uninterrupted supply of diluent, standard solutions, a salt bridge, cuvette wash solution, and probe cleaners. The composition of the various solutions are sufficiently different and susceptible to deterioration that certain of these solutions must be stored in special pouch-like pouches. In particular, the system diluent and fluids associated with the ISE are best stored in multi-ply plastic and metal foil pouches (made from materials such as nylon, low density polyethylene, aluminum foil and the like) in order to minimize oxygen permeability. For this reason, containers 44 and 45 are designed to store solution contained within special collapsible plastic-metal-plastic pouches 63 like seen in FIG. 9 and placed within an opened clam-shell-like container body portion of containers 44 and 45. As explained hereinafter, containers 44 and 45 can be opened in order to place pouch 63 therein and subsequently closed and sealed in order to protect pouch 63 and allow said pouch 63 to be installed within into the appropriate mounting bracket 44P or 45P on analyzer 10.

Figure 9:
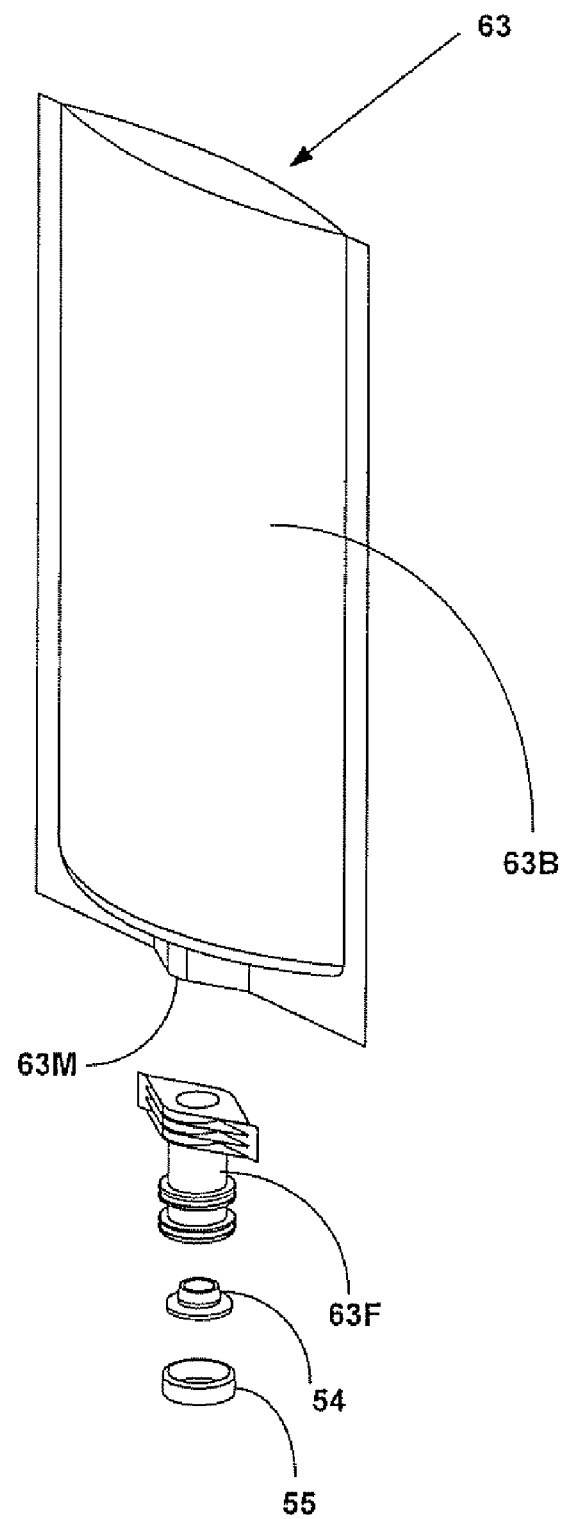
FIG. 9 is an exploded perspective view of a solution pouch of the present invention.

As seen in FIG. 9, pouch 63 comprises a collapsible plastic-metal foil-plastic pouch body 63B having a mouth-like opening 63M, a fitment 64 to be sealed within mouth-like opening 63M, and the septum 54 and open meal band or cap 55 described previously. Fitment 64 may be seen in FIG. 10 and FIG. 10A, as sectional view along lines A-A of FIG. 10, as comprising a generally cylindrical body 64B having a central bore 64R therethrough, best seen in the perspective view of fitment 64 seen on FIG. 10C and in the top plan view FIG. 10D, as well as a number of parallel, spaced apart weld foils or weld sealing foils 64S extending outwardly at a top of body 64B and a pair of seating ridges 64R extending outwardly at a bottom of body 64B and having a groove formed therein. The upper set of ridges 64R is provided for sealing fitment 64 into clam-shell-like thermoformed container 45 and the lower set of ridges 64R is provided for sealing septum 54 onto fitment 64 using cap 55. Weld sealing foils 64S flare outwardly and are tapered to a fin 64F on opposed ends of sealing foils 64S in order to facilitate the integrity of the heat-induced seal within the mouth-like opening 63M of body 63B; for this reason fitment 64 is preferably made of high density polyethylene to satisfy gas diffusion requirements. Seating ridges 64R are designed to mesh within cylindrical open mouth 63M of pouch 63. Septum 54 is illustrated in FIG. 9 and is formed of an elastomer rubber material sized to fit within the interior of fitment 58F thereby sealing liquid contained within pouch body 58B and positioned so that a smooth surface faces outside and a hallowed cup-like surface faces inside pouch 58.

Figure 12:
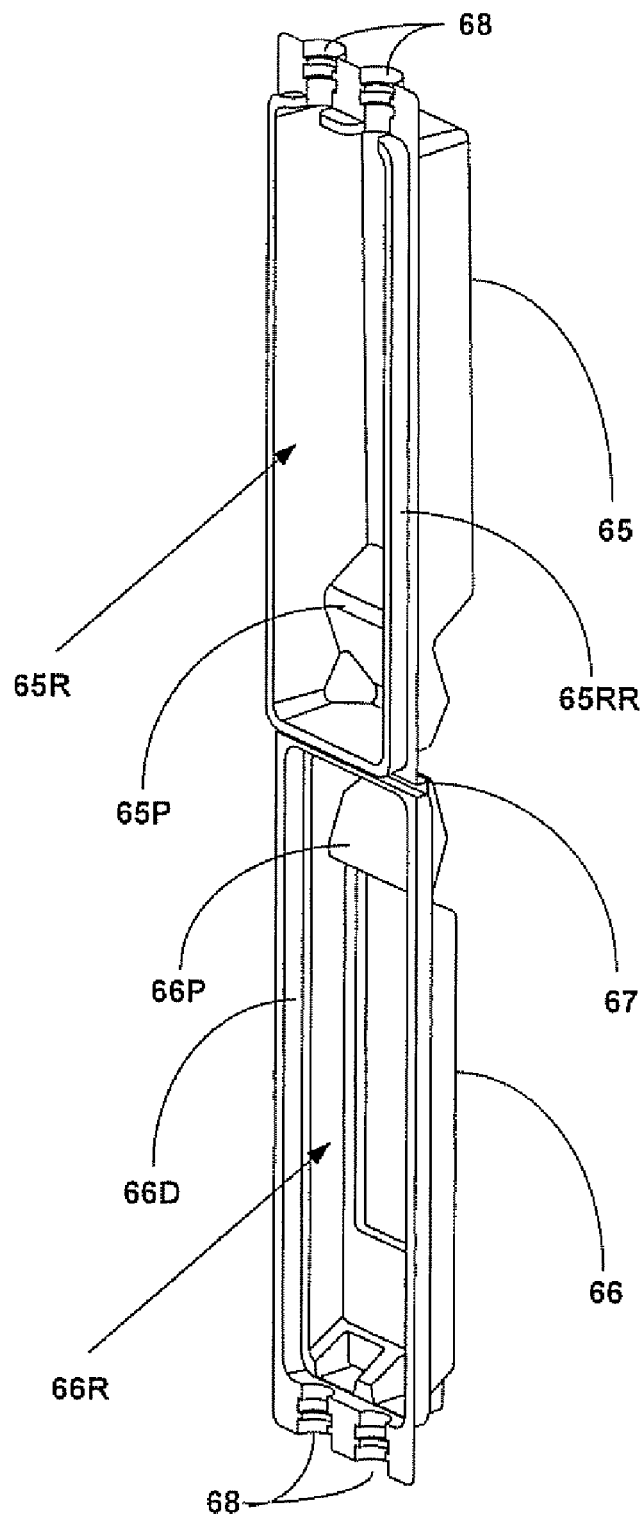
FIG. 12 is an perspective view of details of the bottle-like container of FIG. 11C in an opened form.

Dual chamber clam-shell-like thermoformed polystyrene container 45 (FIG. 11A) is provided for storage and supply of an ISE second standard B solution and salt bridge solution contained in a pair of plastic-metal-plastic pouches 63 like seen in FIG. 11B and placed within an opened clam-shell-like first and second tray-like sections 65 and 66 of container 45 like seen in FIG. 11C. Container 45 is preferably thermoformed in said open clam-shell manner in order to place pouch 63 therein and is subsequently closed and sealed by spot welding in order to protect pouch 63 and allow said pouch 63 to be installed within into the appropriate mounting bracket 44P or 45P on analyzer 10. Pouch 63 has been described as having fitment 64 sealed within mouth-like opening 63M, and the septum 54 sealed thereto using open meal band or cap 55. FIG. 12 illustrates a number of key features of container 45, container 45 comprising a pair of clam-shell-like similarly sized, rectangular shaped first and second tray sections 65, 66 joined at opposing ends by a flexible linear joint 67, both first tray section 65 and second tray section 66 having open recesses 65R and 66R, respectively therein, each recess 65R and 66R sized to accommodate about one-half of a pair of expanded pouches 63. First tray section 65 and second tray section 66 both further comprise a pair of semicircular openings 68 formed in opposing end sections away from linear joint 64J as well as raised portions 65P and 66P, respectively located in recesses 65R and 66R proximate linear joint 67. Both first tray section 65 and second tray section 66 have identical semi-circular openings 68 formed at their opposing ends, the semi-circular openings 68 shaped so that when the first tray section 65 and second tray section 66 are folded or collapsed together like a clam shell, the semi-circular openings 68 mate with one another and form a circular opening within which fitment 63 can be sealed. When first tray section 65 and second tray section 66 are folded together to form a sealed and closed inner shell suitable for holding and protecting pouch 63, raised portions 65P and 66P combine to form a depressed handle 69 suitable for handling by a operator. First tray section 65 further comprise a raised rail 65RR extending continuously or alternately in a broken manner inside the periphery of section 66 and parallel thereto, rail 65RR fitting into a mating depression 65D also formed inside the periphery of section 65 and parallel thereto when first tray section 65 and second tray section 66 are folded together to form a sealed and closed inner shell suitable for holding and protecting pouches 63. Additional engineering details concerning the production and assembly of first tray section 65 and second tray section 66 are incorporated into this specification and are easily understood by one skilled in the art.

Figure 14:
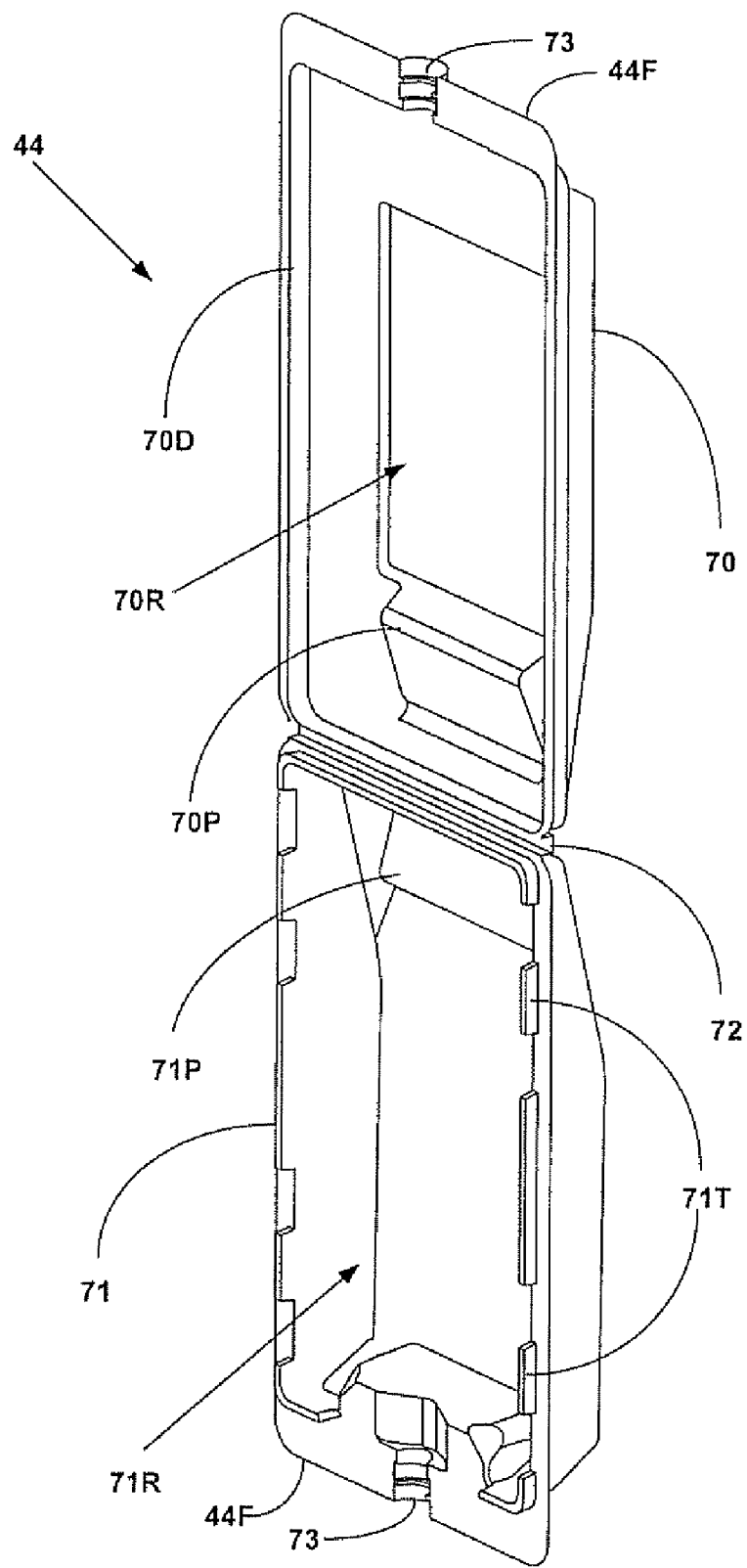
FIG. 14 is an perspective view of details of the bottle-like container of FIG. 13C in an opened form.

Single chamber clam-shell-like polystyrene container 44 (FIG. 13A) is similarly provided for storage and supply of system and ISE diluent as well as for storage and supply of ISE Standard A contained in plastic-metal foil-plastic pouches 63 like seen in FIG. 13B and placed within an opened clam-shell-like first and second tray-like sections 70 and 71 of container 44 like seen in FIG. 13C. Container 44 is similarly thermoformed in said open clam-shell manner in order to place pouch 63 therein and is subsequently closed and sealed in order to protect pouch 63 and allow said pouch 63 to be installed within into the appropriate mounting bracket 44P on analyzer 10. FIG. 14 illustrates a number of key features of container 44, container 44 comprising a pair of clam-shell-like similarly sized, rectangular shaped first and second tray sections 70, 71 joined at opposing ends by a flexible linear joint 72, both first tray section 71 and second tray section 72 having open recesses 70R and 71, respectively therein, each recess 70R and 71R sized to accommodate about one-half of an expanded pouch 63. First tray section 70 and second tray section 71 both further comprise a semicircular opening 73 formed in opposing end sections away from linear joint 72 as well as raised portions 70P and 71P, respectively located in recesses 70R and 71R proximate linear joint 72. Both first tray section 70 and second tray section 71 have identical semi-circular openings 73 formed at their opposing ends, the semi-circular openings 73 shaped so that when the first tray section 70 and second tray section 71 are folded or collapsed together like a clam shell, the semi-circular openings 73 mate with one another and form a circular opening within which fitment 63 can be sealed. For the same reasons, the opposing ends of both first tray section 70 and second tray section 71 are formed as fins 70F and 71F (FIG. 14) so that when the first tray section 70 and second tray section 71 are folded or collapsed together like a clam shell, the fins 70F and 71F mate with one another and form an integral fin 75 (FIG. 13A). When first tray section 70 and second tray section 71 are folded together to form a sealed and closed inner shell suitable for holding and protecting a single pouch 63, raised portions 70P and 71P combine to form a depressed handle 74 (FIG. 13A) suitable for handling by a operator. Second tray section 71 further comprises a number of raised tabs 71T extending in a broken manner inside the periphery of section 71 and parallel thereto, tabs 71T fitting into a mating depression 70D also formed inside the periphery of section 70 and parallel thereto when first tray section 70 and second tray section 71 are folded together to form a sealed and closed inner shell suitable for holding and protecting pouches 63. Importantly, when first tray section 70 and second tray section 71 are folded together, fin sections 70F and 71F align to form an integral fin 75 (FIG. 13A) in which a notch N described hereinafter and indicated by arrow 76 may be cut. Additional engineering details concerning the production and assembly of first tray section 70 and second tray section 71 are incorporated into this specification and are easily understood by one skilled in the art.

Figure 15A:
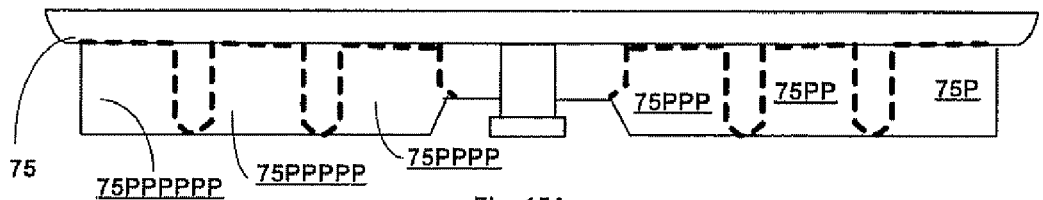
FIGS. 15A-G illustrates several key patterns useful on the bottle-like containers of FIG. 13A.
Figure 15B:
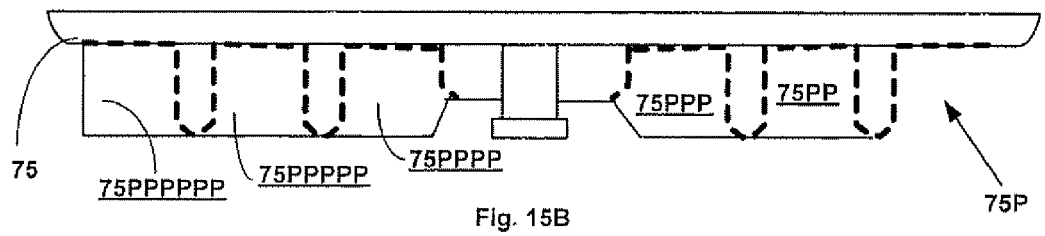
Figure 15C:
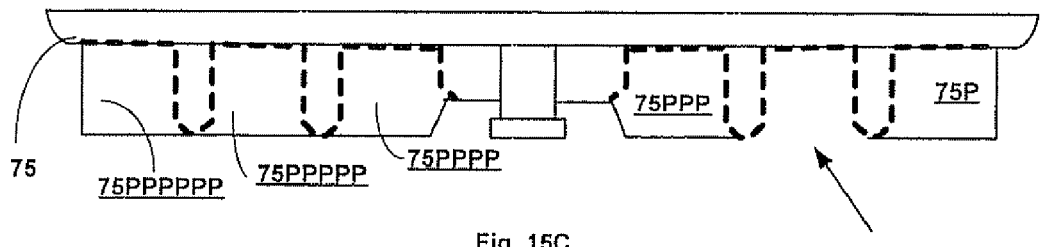
Figure 15D:
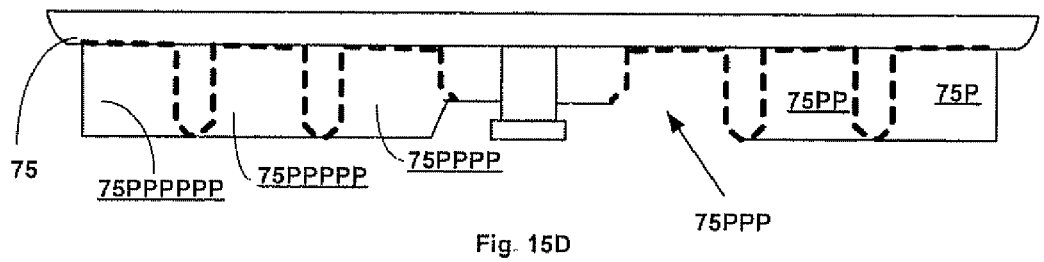
Figure 15E:
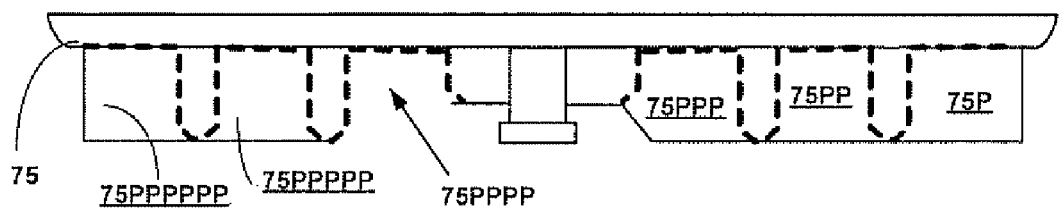
Figure 15F:
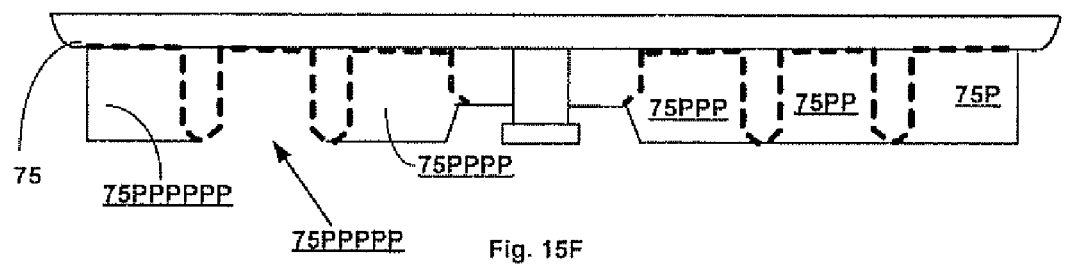
Figure 15G:
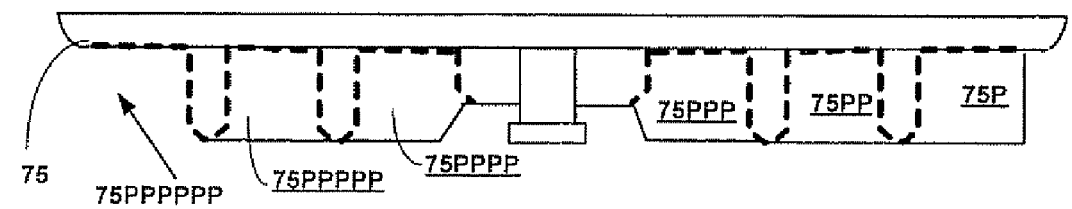
Figure 16:
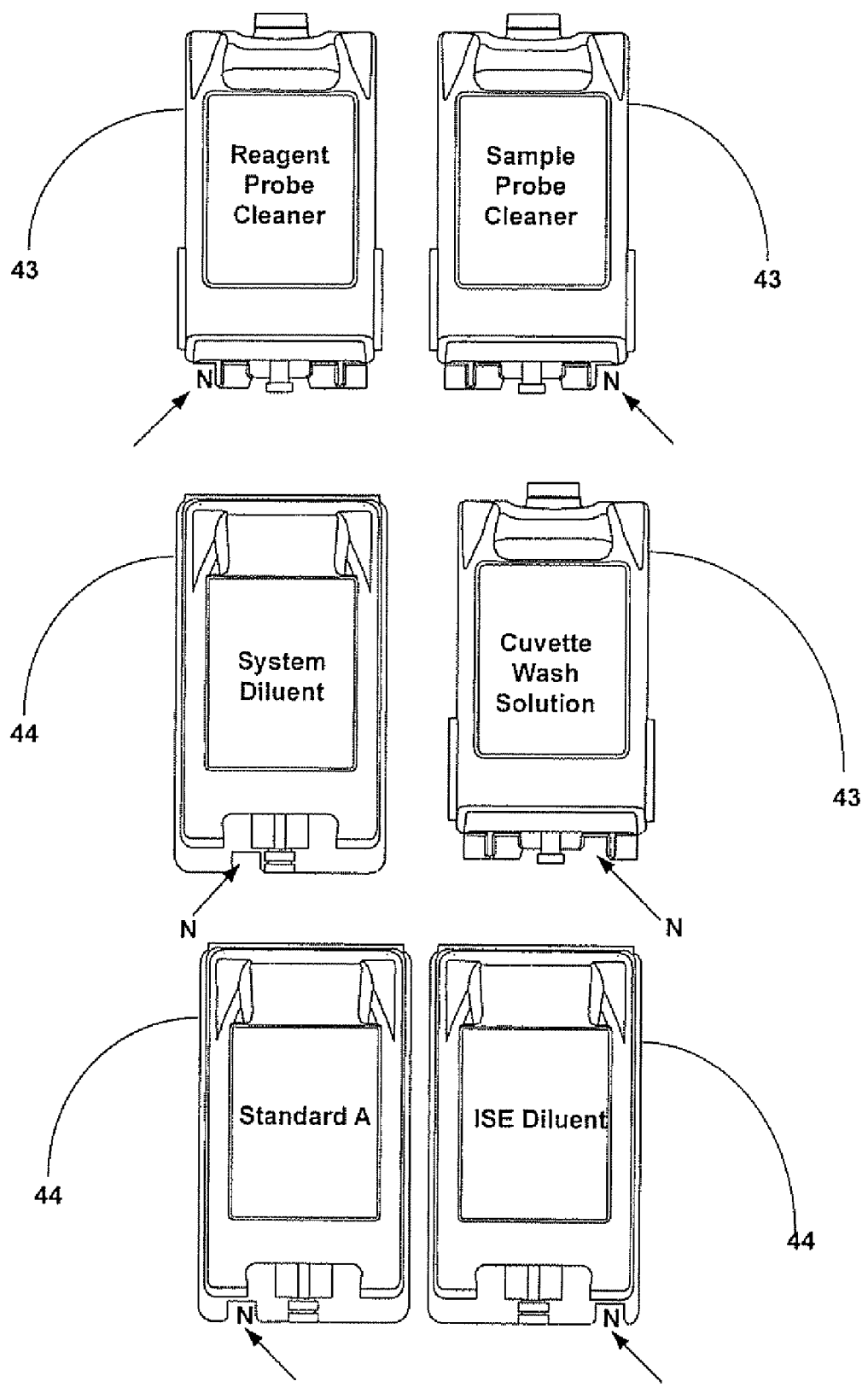
FIG. 16 further illustrates the key patterns of FIGS. 15A-E on the bottle-like containers of FIG. 13A.

As mentioned previously, a key feature of the fluid handling system of the present invention in ensuring that the appropriate bottle container 44 is correctly oriented when placed into appropriate mounting bracket 62M on analyzer 10 is a notching of integral fin 75 in one of six notched patterns, each pattern keyed for a selected solution, mounting bracket 62M having the corresponding keyed pattern so that the only bottle container 44 that can be mounted in mounting bracket 62M has its fin 75 notched in a pattern that corresponds to the mating key pattern 62K. FIG. 15A illustrates fin 75 as comprising a removable first portion 75P having a removable second portion 75PP next adjacent thereto, second portion 75PP having a removable third portion 75PPP next adjacent thereto, third portion 75PPP having a removable fourth portion 75PPPP next adjacent thereto, fourth portion 75PPPP having a removable fifth portion 75PPPPP next adjacent thereto, and fifth portion 75PPPPP having a removable sixth portion 75PPPPPP next adjacent thereto. FIGS. 15B-C-D-E-F-G illustrate one embodiment of this keyed pattern as comprising a first pattern wherein a first portion 75P of fin 75 of container 44 is removed by being cut out (FIG. 15B, for example for containers 44 containing a future clinical solution) and a second pattern wherein a second portion 75PP, next adjacent to first portion 75P of fin 75 is cut out, the first portion 75P remaining intact (FIG. 15C, for example for containers 44 containing ISE diluent solution) and a third pattern wherein a third portion 75PPP next adjacent to second portion 75PP of fin 75 is cut out, the first portion 75P and the second portion 75PP remaining intact (FIG. 15D for example for containers 44 containing a future clinical solution) and a fourth pattern wherein a fourth portion 75PPPP next adjacent to third portion 75PPP of fin 75 is cut out, the first portion 75P and the second portion 75PP and the third portion 75PPP remaining intact (FIG. 15E, for example for containers 44 containing system diluent solution), a fifth pattern wherein a fifth portion 75PPPPP next adjacent to fourth portion 75PPPP of fin 75 is cut out, the first portion 75P and the second portion 75PP and the third portion 75PPP remaining intact (FIG. 15F, for example for containers 44 containing ISE first standard A solution), and a sixth pattern wherein a sixth portion 75PPPPPP next adjacent to fifth portion 75PPPPP of fin 75 is cut out, the first portion 75P and the second portion 75PP and the third portion 75PPP and the fourth portion 75PPPP and the fifth portion 75PPPPP remaining intact (FIG. 15G, for example for containers 44 containing a future clinical solution). FIG. 16 is presented as exemplary of the previously described containers 43 and 44 having solution identifying keyed patterns as described therefore and in which an arrow successively points to the identifying notch N pattern. Those skilled in the art will readily appreciate that other keyed patterns may be cut out for fin 75, and that the removal of portions 75P, 75PP, 75PPP, and 75PPPP may be altered without departing from the scope of the invention. In the embodiment shown, all of portions 75P, 75PP, 75PPP, and 75PPPP were removed sequentially. However, in alternate embodiments, selected pairs or other groups of portions 75P, 75PP, 75PPP, and 75PPPP may be removed without departing from the scope of the invention.

FIG. 17 illustrates mounting bracket 62M-ISE (in transparent dashed lines for clarity) have a unique mating key pattern 62K-ISE, for example so that only containers 44 containing system diluent solution and having fourth portion 75PPPP cut out can be mounted therein. FIG. 17A further illustrates mounting bracket 62M-SPC (in transparent dashed lines for clarity) as having a unique mating key pattern 62K-SPC, for example, so that only the containers 43 containing sample probe cleaner solution and having first portion 60P cut out can be mounted therein. To one skilled in the art, it is apparent that a unique mating key pattern 62K can be created for at least each of the three containers 43 having different sample and reagent probe cleaning solutions and cuvette wash solution therein and that a unique mating key pattern 62K can be created for at least each of the three containers 44 having different diluent solutions, and first standard solution therein. For example, selected pairs or other groups of portions 75P, 75PP, 75PPP, 75PPPP, 75PPPPP and 75PPPPPP may be removed and/or selected pairs or other groups of portions 60P, 60PP, 60PPP, and 60PPPP may be removed so that any number of different solution containers may be uniquely created and uniquely mated to different mounting brackets 62M without departing from the substance or scope of the present invention.

Figure 18B:
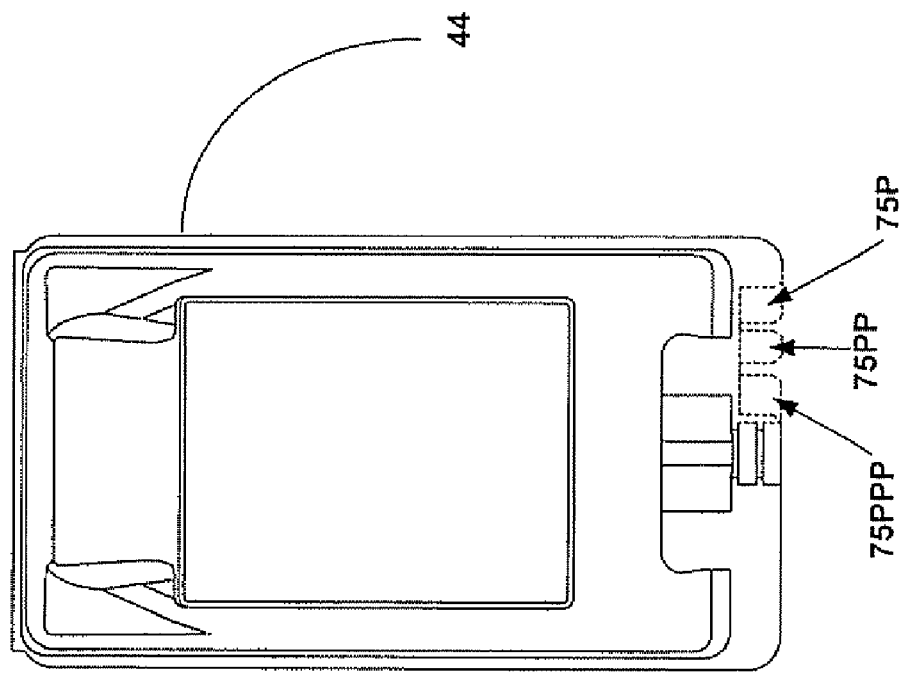
FIG. 18B illustrates an alternate embodiment of FIG. 15A-G.
Figure 18A:
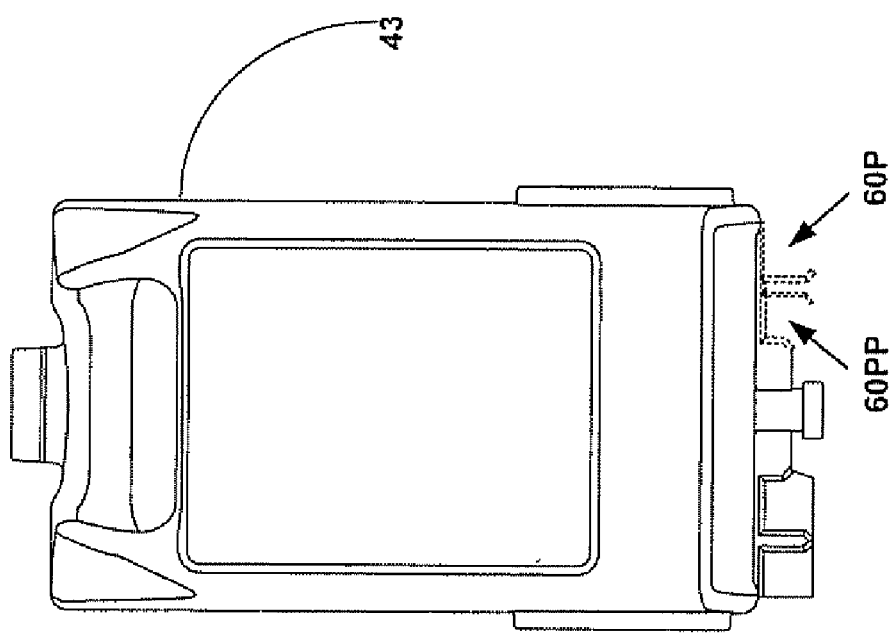
FIG. 18A illustrates an alternate embodiment of FIG. 7A-E.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. In particular, FIGS. 7B-C-E-D-E and 15B-C-D-E-F-G has illustrated notches 60P, 60PP, 60PPP, and 60PPPP as being distinct from one another without overlapping. Similarly, 15B-C-D-E-F-G has illustrated notches 75P, 75PP, 75PPP, 75PPPP, 75PPPPP and 75PPPPPP as being distinct from one another without overlapping. It should be appreciated that these notches could overlap one another and achieve the same unique key patterns. FIG. 18A is illustrative of such an embodiment wherein notches 60P and 60PP are shown (in dashed lines for purposes of clarity) as slightly overlapping. Similarly, FIG. 18B is illustrative of such an embodiment wherein notches 75P, 75PP, and 75PPP are shown (in dashed lines for purposes of clarity) as slightly overlapping.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. An automatic clinical analyzer having a fluid handling system for storing and supplying a number of liquid solutions consumed therein, the analyzer comprising:
   - a reaction carousel supporting reaction cuvettes for containing assay mixtures;
   - a plurality of probes for supplying sample and reagent mixtures into the cuvettes;
   - a plurality of assay operational devices that operate on the sample and reagent mixtures in the cuvettes;
   - a plurality of detector units to perform clinical analytical measurements on the sample and reagent mixtures in the cuvettes;
   - a plurality of different containers that contain sample and reagent probe cleaners, a system diluent, or a reaction cuvette wash solution, each container having opposed top and a bottom surfaces, the bottom surface includes a front tapered portion with a mounting fin and an opening depending therefrom, each of the mounting fins having a different pattern of at least one open notch therein, each container further including opposed side surfaces and opposed front and back surfaces, the opposed side surfaces having alignment ridges extending therefrom and positioned between a centerline of the side surfaces and the front surface; and a plurality of container mounting brackets, each bracket having a mating key with a pattern of closed and open sections that match only one of the open notch patterns in the mounting fins so that only one of the different containers can be mounted in each of the container mounting brackets.

2. The clinical analyzer of claim 1, wherein the alignment ridges are sized to fit into corresponding grooves formed in a mounting bracket.

3. The clinical analyzer of claim 1, wherein the pattern of at least one open notch comprises a number of overlapping notches.

4. The clinical analyzer of claim 1, further comprising a collapsible plastic-foil-plastic pouch contained within at least one of the containers.

5. The clinical analyzer of claim 4, wherein the pouch comprises an opening, a fitment to be sealed within the opening, a septum within the fitment, and a metal cap to seal the septum into the fitment.

6. The clinical analyzer of claim 5, wherein the fitment comprises a generally cylindrical body having a central bore therethrough, a number of parallel, spaced apart weld sealing foils extending outwardly at a top portion of the body, and a pair of seating ridges extending outwardly at a bottom portion of the body and having a groove formed therein.

7. The clinical analyzer of claim 6, wherein the weld sealing foils flare outwardly and are tapered to a fin on opposed ends of the weld sealing foils in order to facilitate the integrity of a heat-induced seal within the mouth-like opening of the pouch.

8. The clinical analyzer of claim 5, wherein the fitment is sized to fit within the opening of the container.

* * * * *